US007003876B2

(12) United States Patent
Crawford et al.

(10) Patent No.: US 7,003,876 B2
(45) Date of Patent: Feb. 28, 2006

(54) METHOD OF CONSTRUCTING AN IN THE EAR AUXILIARY MICROPHONE FOR BEHIND THE EAR HEARING PROSTHETIC

(75) Inventors: Scott A. Crawford, Castaic, CA (US); C. Geoffrey E. Fernald, La Canada, CA (US)

(73) Assignee: Advanced Bionics Corporation, Valencia, CA (US)

( * ) Notice: Subject to any disclaimer, the term of this patent is extended or adjusted under 35 U.S.C. 154(b) by 224 days.

(21) Appl. No.: 10/731,049

(22) Filed: Dec. 9, 2003

(65) Prior Publication Data
US 2004/0114776 A1 Jun. 17, 2004

Related U.S. Application Data

(62) Division of application No. 09/927,130, filed on Aug. 10, 2001, now Pat. No. 6,775,389.

(51) Int. Cl.
H01R 43/00 (2006.01)
(52) U.S. Cl. .............. 29/859; 29/825; 29/857; 29/858
(58) Field of Classification Search ......... 29/825, 29/857, 858, 859
See application file for complete search history.

(56) References Cited

U.S. PATENT DOCUMENTS 4,696,287 A    9/1987  Hortman et al.
5,535,282 A    7/1996  Luca
5,701,348 A   12/1997  Shennib et al.
5,757,933 A    5/1998  Preves et al.
5,782,744 A    7/1998  Money
5,790,672 A    8/1998  Klostermeir
5,814,095 A    9/1998  Muller et al.
5,824,022 A   10/1998  Zilberman et al.
5,906,635 A    5/1999  Maniglia
6,161,046 A   12/2000  Maniglia et al.
6,216,040 B1   4/2001  Harrison
6,259,951 B1   7/2001  Kuzma et al.
6,272,382 B1   8/2001  Faltys et al.
6,308,101 B1  10/2001  Faltys et al.

FOREIGN PATENT DOCUMENTS

DE         3502178 A1    8/1985
WO      WO-01/56521 A1   8/2001

Primary Examiner—Carl J. Arbes
(74) Attorney, Agent, or Firm—Kenneth L. Green; Peter K. Johnson; Philip H. Lee

(57) ABSTRACT

An In The Ear (ITE) microphone improves the acoustic response of a Behind The Ear (BTE) Implantable Cochlear Stimulation (ICS) system during telephone use. An acoustic seal provided by holding a telephone earpiece against the ear provides improved coupling of low frequency (up to about 1 KHz) sound waves, sufficient to overcome losses due to the near field acoustic characteristics common to telephones. In a preferred embodiment, the ITE microphone is connected to a removable ear hook of the BTE ICS system by a short bendable stalk.

20 Claims, 4 Drawing Sheets

METHOD OF CONSTRUCTING AN IN THE EAR AUXILIARY MICROPHONE FOR BEHIND THE EAR HEARING PROSTHETIC

The present application is a Divisional of U.S. application Ser. No. 09/927,130, filed Aug. 10, 2001 now U.S. Pat. No. 6,775,389, which application is incorporated herein by reference in its entirety.

BACKGROUND OF THE INVENTION

The present invention relates to hearing devices for aiding the hearing impaired and the profoundly deaf, and more particularly to an In The Ear (ITE) auxiliary microphone connected to a Behind The Ear (BTE) speech processor through a removable ear hook. The microphone of the present invention is especially useful for a user conversing over a telephone.

Implantable Cochlear Stimulation (ICS) systems are known in the art. Such systems are used to help the profoundly deaf (those whose middle and/or outer ear is dysfunctional, but whose auditory nerve remains intact) to hear. The sensation of hearing is achieved by directly exciting the auditory nerve with controlled impulses of electrical current, which impulses are generated as a function of perceived audio sounds. The audio sounds are picked up by a microphone carried externally (not implanted) by the deaf person and converted to electrical signals. The electrical signals, in turn, are processed and conditioned by a Wearable Signal Receiver and Processor (WP) in an appropriate manner, e.g., converted to a sequence of pulses of varying width and/or amplitude, and then transmitted to an implanted receiver circuit of the ICS system. The implanted receiver circuit generates electrical current as a function of the processed signal it receives from the WP (which in turn is based on the audio sounds picked up by the external microphone). The implanted receiver circuit is connected to an implantable electrode array that has been implanted into the cochlea of the inner ear. The electrical current generated by the implanted receiver circuit is applied to individual electrode pairs of the electrode array. It is this electrical current which directly stimulates the auditory nerve and provides the user with the sensation of hearing.

While known ICS systems have succeeded in providing hearing to the deaf, ICS systems also have the disadvantage of appearing unsightly. ICS systems include an external headpiece, positioned on the side of the user's head, and require an external cable running from the external headpiece to the WP. The WP is typically worn or carried by the user on a belt or in a pocket. While the WP is not too large, it is likewise not extremely small, and hence also represents an inconvenience for the user. The cable which connects the WP with the headpiece is particularly a source of irritation and self-consciousness for the user.

The above-described aesthetic considerations and inconvenience of an external wire are addressed by U.S. Pat. No. 5,824,022, issued Oct. 20, 1998, for "Cochlear Stimulation System Employing Behind-The-Ear (BTE) Speech Processor With Remote Control." The '022 patent teaches a small single external device that performs the functions of both the WP and the headpiece. The external device is positioned behind the ear to minimize its visibility, and requires no cabling to additional components. The '022 patent is incorporated herein by reference.

While the BTE device taught by the '022 patent resolves the issues of aesthetics and inconvenience, the placement of the microphone in the BTE device case results in poor microphone performance when using a telephone. The near field acoustic characteristics of known telephones, and the absence of a seal between the telephone earpiece and the microphone in the BTE case, degrades the coupling of low frequency information up to about 1 KHz. Further, known ICS systems and hearing aids use a telecoil residing near the earpiece of a telephone handset to detect the magnetic field produced by the speaker in the handset, however, low magnetic field phones and cell phones using piezo transducers, do not couple well with telecoils.

Therefore, there is a need to improve the performance of known ICS systems when the user is conversing over a telephone.

SUMMARY OF THE INVENTION

The present invention addresses the above and other needs by providing an In The Ear (ITE) microphone that improves the acoustic response of a Behind The Ear (BTE) Implantable Cochlear Stimulation (ICS) system during telephone use. An acoustic seal provided by holding a telephone earpiece against the outer ear provides improved coupling of low frequency (up to about 1 KHz) sound waves, sufficient to overcome losses due to the near field acoustic characteristics resulting from the telephone microphone cooperation. In a preferred embodiment, the ITE microphone is connected to a removable ear hook of the BTE ICS system by a short bendable stalk.

In accordance with one aspect of the invention, there is provided an ITE microphone for a BTE ICS system, which microphone is placed within the concha of the ear. When a telephone handset is held against the ear, the phone seals against the outer ear, creating a chamber wherein the microphone resides. Sealing the microphone within such chamber results in improved frequency fidelity due to the sealing in of the sound pressure. Such sealing also reduces the amount of outside noise that reaches the microphone. Advantageously, the BTE ICS system does not require any earmolding to provide adequate sealing. Further, the positioning of the microphone within the ear improves hearing by using the natural acoustics of the ear.

It is a further feature of the invention to provide a BTE ICS system that works equally well with low magnetic field phones and cell phones using piezo transducers which do not couple well to a telecoil. The ITE microphone relies entirely on the acoustic signal transmitted by the speaker in the telephone handset, which speaker is designed to achieve the acoustic performance objectives of the unaided hearing population. The performance of the BTE ICS system using the ITE microphone is therefore unaffected by the type of speaker (or sound transducer) used in the telephone handset.

It is an additional feature of the present invention, that when exercised in conjunction with an ICS system, there is no acoustic feedback from a microphone to affect performance. Conventional hearing aids use a speaker in the user's ear to broadcast an amplified acoustic signal to the user. If an ITE microphone was used in the same ear, the result would be severe acoustic feedback. The present invention is applied to ICS systems, wherein the output of the ICS system is electrical stimulation of the cochlea, not an acoustic signal.

It is a further additional feature that use of the ITE microphone does not result in chafing to the skin of the ear. The ITE microphone of the present invention includes a bendable stalk, which stalk retains a shape once the stalk is bent into that shape. The stalk may thus be bent to avoid rubbing against the skin of the ear, and the resulting chafing of the skin.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
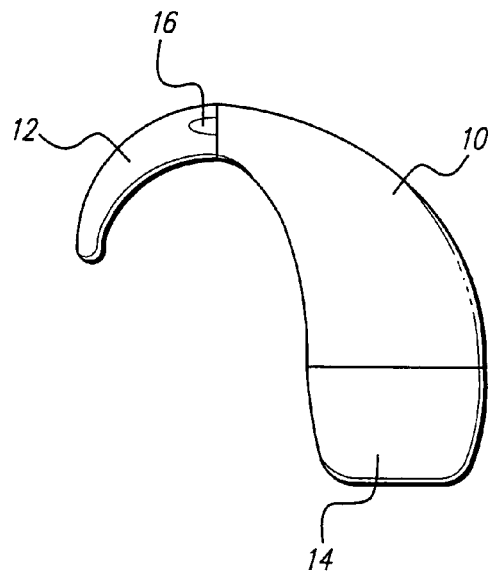
FIG. 1A depicts a prior art BTE device and earhook.
Figure 1B:
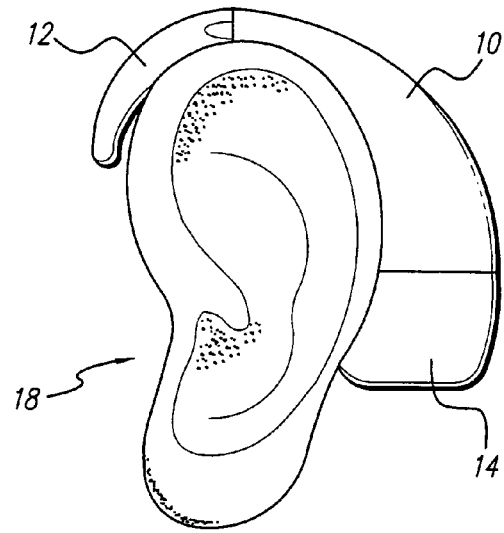
FIG. 1B depicts the prior art BTE device and earhook placed upon the ear of a user.

The In The Ear (ITE) microphone of the present invention improves the acoustic response of a Behind The Ear (BTE) Implantable Cochlear Stimulation (ICS) system during telephone use. As shown in FIG. 1A, when combined (or connected together), a prior art earhook 12 and BTE device 10 of an ICS system resemble a common BTE hearing aid. The earhook 12 is arched and hooks in front of the ear. The BTE device 10 continues the arch to the rear of the ear and is positioned behind the ear. A battery compartment 14 is removably attached to the bottom of the BTE device 10. Various batteries of different sizes may be interchangeably attached to the BTE device 10 depending upon the needs of a user. A more detailed description of a BTE device may be found in U.S. Pat. No. 5,824,022, previously incorporated herein by reference. In known BTE devices 10, a BTE microphone is positioned in the case of the BTE device 10 behind a microphone port 16. The earhook 12 typically defines a recess cooperating with the port 16 to facilitate the communication of sound waves with the BTE microphone. The BTE device 10 with the earhook 12 attached, is shown residing on an ear 18 in FIG. 1B.

Figure 1C:
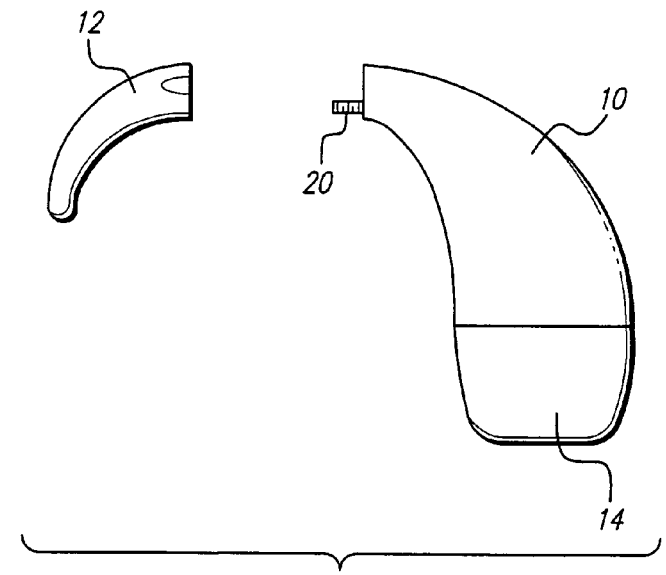
FIG. 1C shows the prior art BTE device and earhook with the earhook detached from the BTE device.

Turning to FIG. 1C, a coaxial connector 20 is shown attached to the BTE device 10. Such co-axial connector 20 is disclosed in currently pending U.S. patent application Ser. No. 09/785,629 filed Feb. 16, 2001 for "Connector System for BTE Hearing Devices." The coaxial connector 20 serves as both an attaching fixture for the standard earhook 12 and special earhooks (i.e., provides a mechanical connection), and as an electrical connector for auxiliary devices (i.e., provides an electrical connection between the BTE electronics circuits and other electronic devices or sensors included within, or attached to, an earhook). Advantageously, the dual use feature of the coaxial connector 20 eliminates the need to provide a separate connector for connecting (electrically or mechanically) auxiliary devices to the BTE device 10. The '629 application teaches the construction and use of the co-axial connector to mechanically and electrically connect a special earhook to a BTE device 10. The '629 application also discloses several special earhooks intended to add features to the BTE ICS device. The '629 application does not however contemplate a special earhook which provides an ITE microphone. The '629 application is herein incorporated by reference.

Figure 2:
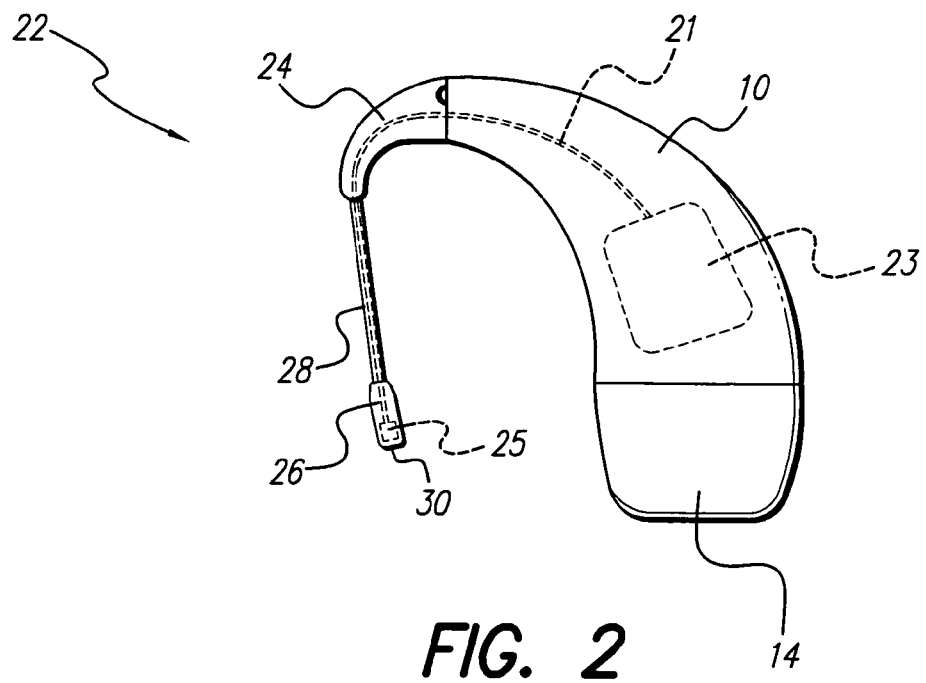
FIG. 2 shows the BTE device with the In The Ear (ITE) microphone attached.

An ITE microphone earhook 22 is shown attached to the BTE device 10 in FIG. 2. The ITE microphone earhook 22 comprises a second earhook 24, a microphone assemble 26, and a stalk 28 mechanically and electrically connecting the microphone assemble 26 to the earhook 24. The microphone assemble 26 includes a soundport 30 defined at a distal end of the microphone assemble 26. The stalk 28 preferably is bendable and preferably retains a position into which the stock 28 is bent. In a preferred embodiment, the ITE microphone earhook 22 is attached to the BTE device 10 using the coaxial connector 20 of the '629 patent, however, those skilled in the art will recognize that a variety of apparatus and methods of attaching an ITE microphone to a BTE device are available. Further, the ITE microphone 25 need only be electrically connected 21 to the speech processor 23 of an ICS system, including a BTE system, and may include other means to secure the ITE microphone (e.g., any means that might be used to secure a common earphone may prove suitable to secure the ITE microphone) in place. These other means for connecting the ITE microphone to the BTE device are intended to come within the scope of the present invention.

Figure 3:
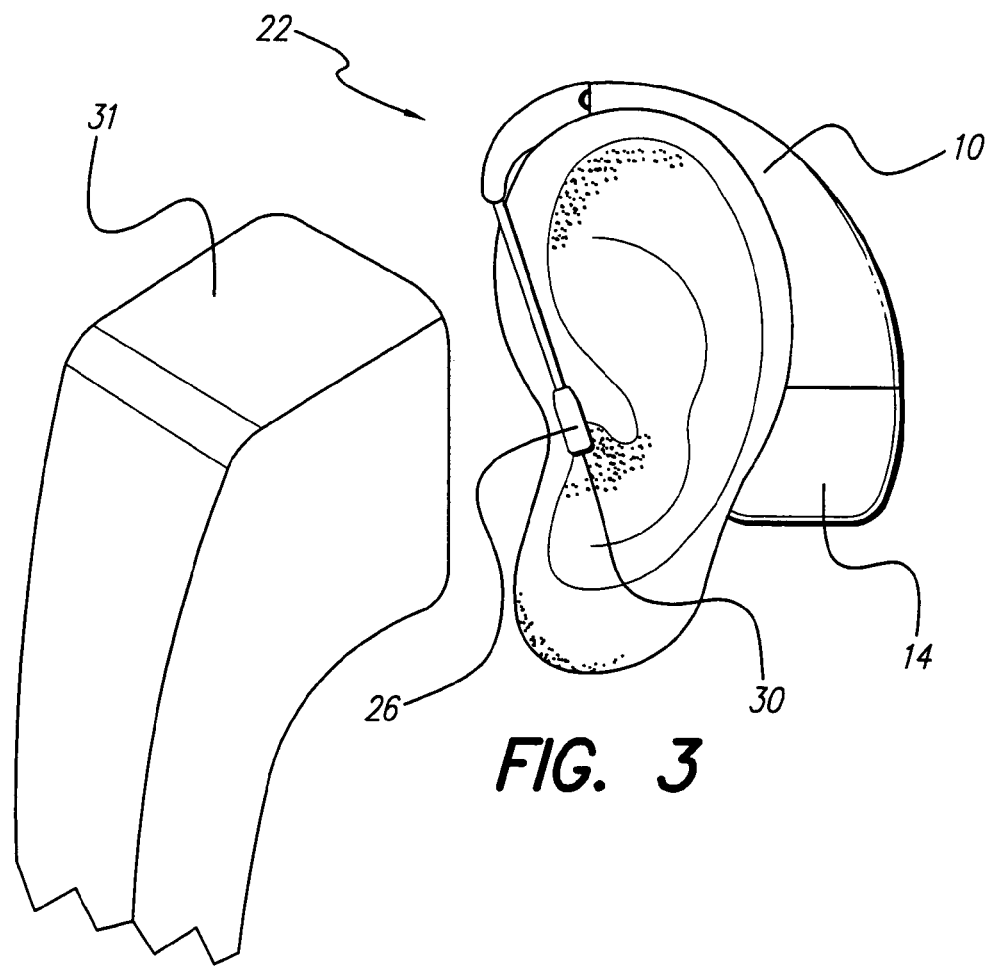
FIG. 3 depicts the BTE device with ITE microphone attached placed upon the ear of a user.

The ITE microphone earhook 22 and BTE device 10 are shown residing on the ear of a user in FIG. 3. The microphone assemble 26 preferably resides behind the tragus and directed towards the concha of the ear, with the soundport 30 facing downward and somewhat rearward. Some users may vary location of the microphone assemble 26, and these variations are intended to come within the scope of the present invention. The soundport 30 receives sound waves and is open to the volume between the earpiece 31 of a communications handset, such as a telephone handset, and the ear of a user.

Figure 4:
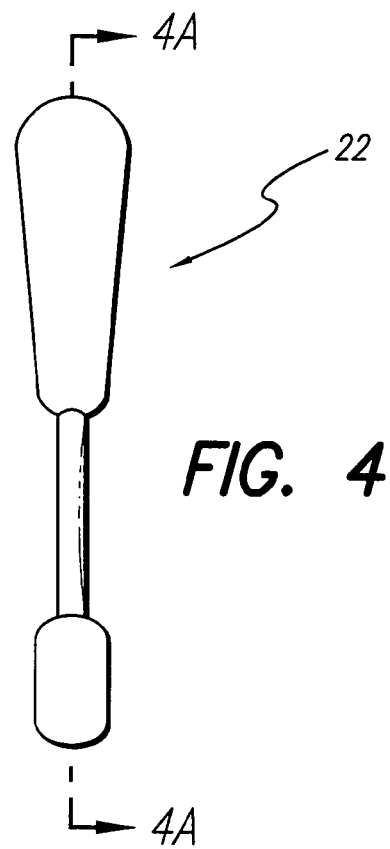
FIG. 4 shows a front view of the ITE microphone and earhook.
Figure 4A:
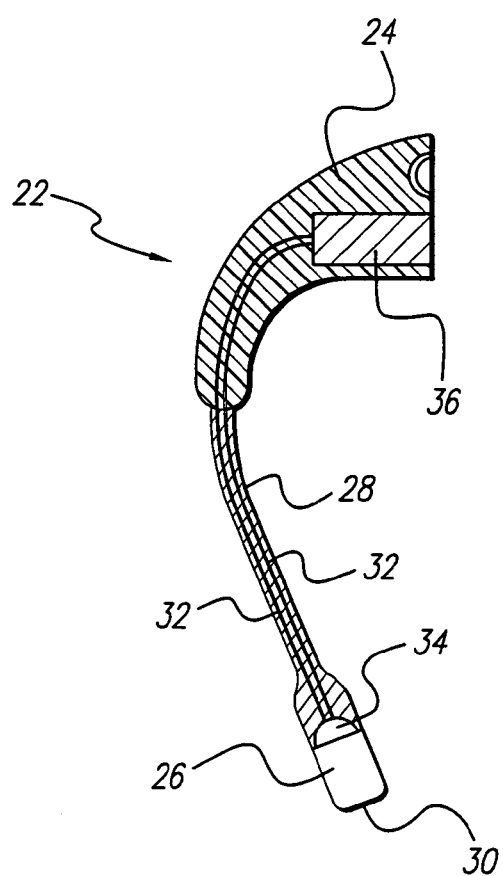
FIG. 4A shows a cross-sectional view of the ITE microphone and earhook taken along line 4A—4A of FIG. 4.

A front view of the ITE microphone earhook 22 is shown in FIG. 4, and a cross-sectional view of the ITE microphone earhook 22 taken along line 4A—4A of FIG. 4 is shown in FIG. 4A. A mating connector 36 is shown residing in the earhook 24. Such mating connector may be any connector suitable to electrically and mechanically connect the earhook 24 to the BTE device 10. Preferably, the mating connector 36 is the mating connector described in the '629 application. Those skilled in the art will recognize that other connectors may be used to connect the earhook 24 to the BTE device 10, including separate connectors for mechanical and electrical connecting. A microphone 34 resides in the microphone assemble 26, and is connected by at least one conductor 32 to the mating connector 36. While the conductor 32 preferably is electrically connected to the mating connector 36, in other embodiments the conductor 32 may be electrically connected to an electrical connector independent of the mating connector 36, or may exit the ITE microphone earhook 22 and electrically connect to a connector on the exterior of the BTE device 10.

Figure 5:
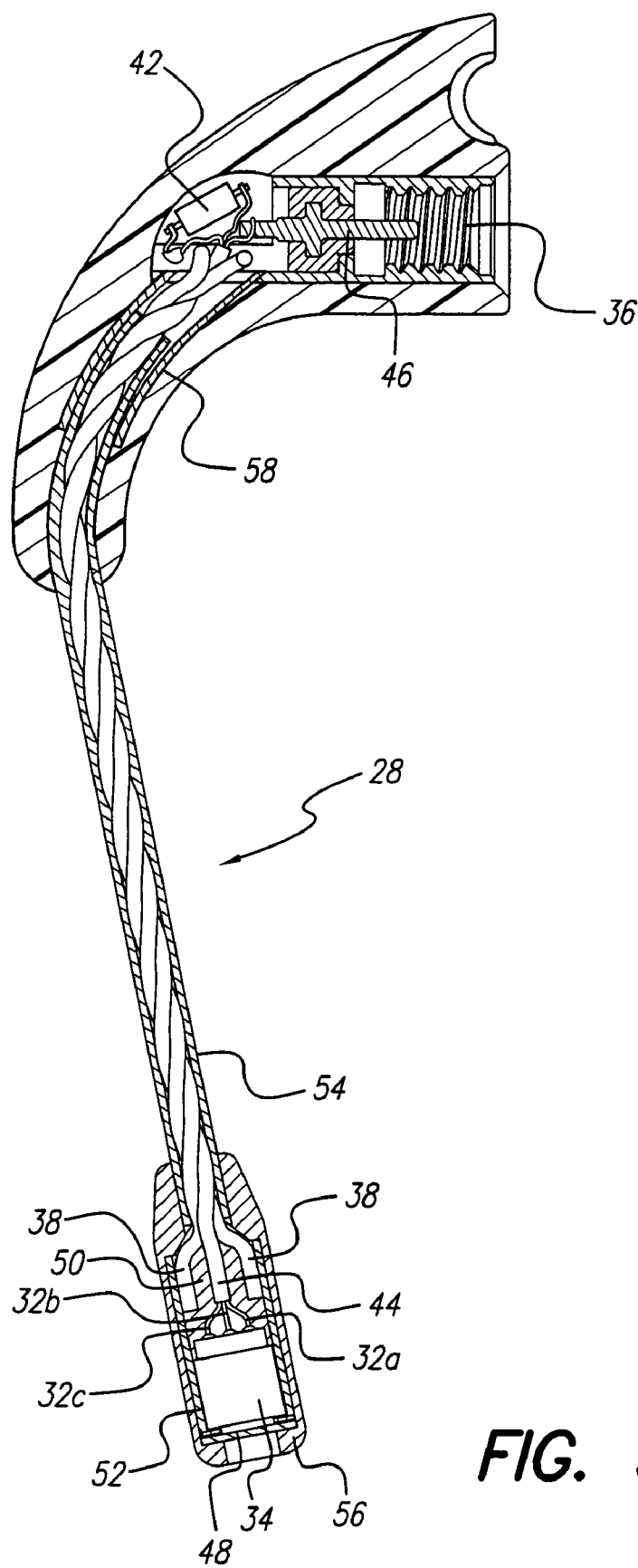
FIG. 5 shows a cross-sectional view of a preferred embodiment of the ITE microphone and earhook taken along line 4A—4A of FIG. 4.

A cross-sectional view of a preferred embodiment of the ITE microphone earhook 22, taken along line 4A—4A of FIG. 4, is shown in FIG. 5. The microphone 34 resides in a sleeve 52, wherein the sleeve 52 is preferably made from brass. A filter 48 seals the microphone 34 from the environment, while letting sound pass to the microphone 34. In a preferred embodiment, the microphone 34 comprises an FG Series microphone manufactured by Knowles Electronics Inc. in Itasca, Ill., and preferably an FG3329. The FG3329 microphone is operated in a two wire mode using a bias setting resistor 42. The at least one conductor 32 comprises three conductors 32a, 32b, and 32c attached at a distal end of the stalk 28 to three terminals on the FG3329 microphone. One of the three conductors 32a, 32b, and 32c is electrically connected to a contact 46 in the center of the mating connector 36, and two of the three conductors 32a, 32b, and 32c are connected to the bias setting resistor 42, and to the body of the mating connector 36. The three conductors 32a, 32b, and 32c are carried in a single cable 44, and the cable 44 is wound with two stiffening members 38, which stiffening members 38 are preferably made from wire, more preferably from zinc or copper. The stiffening members 38 enable the stalk 28 to be bent into a desired shape, and to retain the shape. The wound combination of the cable 44 and the stiffening members 38 is covered by shrink tubing 54. The stiffening members 38 allow the stalk 28 to be bent into various shapes to better fit a user, and to retain such shapes. The stiffening members 38 are connected to the sleeve 52. The stiffening members 38 provide the stalk 28 with the ability to be bent and to retain the position into which the stock 28 is bent. The volume 50 behind the microphone 34 is filled with potting compound to prevent the conductors 32a, 32b, and 32c from flexing and detaching from the microphone 34 when the stalk 28 is adjusted. The entire assembly including the microphone 34, sleeve 52, and conductors 32a, 32b, and 32c, is covered by a boot 56, preferably molded from an elastomer.

A method of constructing the ITE microphone earhook 22 is as follows. The conductors 32a, 32b, and 32c are soldered to terminals on the microphone 34 to form a first subassembly. The stiffening members 38 are soldered to the sleeve 52 to form a second sub-assembly. The first subassembly is inserted into the second sub-assembly, wherein the conductors 32a, 32b, and 32c are guided into the end of the sleeve 52 opposite the stiffening members 38, until the end of the microphone 34 opposite the conductors 32a, 32b, and 32c is flush with the end of the sleeve 52 opposite the stiffening members 38. The resulting cavity in the sleeve 52 containing the conductors 32a, 32b, and 32c is filled with potting compound and allowed to cure. (This creates a solid structure of the microphone, cable, sleeve and flexible members so that any bending in the stalk will not be transferred to the solder joints of the conductors 32a, 32b, and 32c that would weaken and eventually fail the connection.) After curing of the potting compound, the stiffening members 38 and the cable 44 are twisted together as a group to about 3 turns per inch. Shrink tubing 54 is applied over the stiffening members 38 and the cable 44, up to the base of the sleeve 52, to form the ITE microphone stalk 28. The filter 48 is attached to the end of the sleeve 52 opposite the stalk 28 to protect the microphone 34 from moisture. The microphone 34 and stalk 28 assembly is then inserted, stalk 28 first, through the large opening of the microphone boot 56. The microphone boot 56 will stretch over the sleeve 52 and encapsulate the entire microphone assembly. The curved tube 58 is soldered to the mating connector 36, and the stalk 28 is inserted into the curved tube 58. The proper length of the stalk 28 is determined, and the two stiffening members 38 are then soldered to the inside diameter of the mating connector 36 for a mechanical connection. The conductors 32a, 32b, and 32c are then soldered to the appropriate terminals of the mating connector 36 and the resistor 42. After soldering is completed, the volume around the soldered connections is potted with epoxy to cover the connections and the resistor 42 to protect them from damage during the over mold process of the ear hook. The mating connector 36, curved tube 58, and adjacent end of the stalk 28 are over molded with a medical grade PVC to form the ear hook to complete the ITE microphone earhook 22.

An ITE microphone for use with BTE ICS systems has been described. The ITE microphone resides within a sealed chamber formed by the telephone, or other communications device, handset earpiece, and the ear. As a result of sealing in the sound waves, the low frequency near field acoustic degradation otherwise experienced by the user are substantially mitigated, and a significant improvement in the quality of the sound perceived by the ICS system user results. The ITE microphone performs equally well with traditional telephones and with low magnetic field phones and cell phones using piezo transducers which do not couple well with telecoils.

While the invention herein disclosed has been described by means of specific embodiments and applications thereof, numerous modifications and variations could be made thereto by those skilled in the art without departing from the scope of the invention set forth in the claims.

What is claimed is:

1. A method of constructing an ITE microphone earhook, comprising:

attaching at least one conductor to at least one terminal on a microphone;

electrically connecting at least one of the at least one conductor to at least one contact of a mating connector;

carrying the at least one conductor within at least one cable;

winding the at least one cable with at least one stiffening member;

covering the wound at least one cable and at least one stiffening member with shrink tubing;

filling the volume surrounding the at least one attachment of the at least one conductor and the at least one terminal on the microphone with potting compound; and covering the microphone and the at least one conductor with a boot.

2. The method of claim 1 further comprising electrically connecting at least one of the at least one conductor to a bias setting resistor and the body of the mating connector.

3. The method of claim 1 further comprising connecting the at least one stiffening member to a sleeve.

4. The method of claim 3, wherein the step of filling the volume surrounding the at least one attachment of the at least one conductor and the at least one terminal on the microphone with potting compound further comprises filling the volume surrounding the at least one attachment of the at least one conductor and the at least one terminal on the microphone and the volume surrounding the at least one connection of the at least one stiffening member to the sleeve with potting compound.

5. The method of claim 3, wherein the step of covering the microphone and the at least one conductor with a boot further comprises covering the microphone, the sleeve, and the at least one conductor with a boot.

6. A method of constructing an ITE microphone earhook, comprising:
   attaching at least one conductor to at least one terminal on a microphone to form a first sub-assembly;
   attaching at least one stiffening member to a sleeve to form a second sub-assembly;
   inserting the first sub-assembly into the second sub-assembly;
   filling the resulting cavity in the sleeve containing the at least one conductor with potting compound;
   twisting the at least one stiffening member and the at least one conductor together;
   sliding shrink tubing over the at least one stiffening member and the at least one conductor to form a stalk;
   attaching a filter to the end of the sleeve opposite the stalk;
   inserting the microphone and stalk through the opening of a microphone boot;
   soldering a curved tube to a mating connector;
   inserting the stalk into the curved tube;
   soldering the at least one conductor to at least one terminal of the mating connector to form at least one connection; and
   over molding the mating connector, curved tube, and adjacent end of the stalk.

7. The method of claim 6 wherein attaching at least one conductor to at least one terminal on a microphone comprises attaching three conductors to three terminals on a microphone to form a first sub-assembly.

8. The method of claim 6 wherein attaching at least one stiffening member to a sleeve comprises attaching two stiffening members to a sleeve to form a second sub-assembly.

9. The method of claim 6 wherein attaching at least one stiffening member to a sleeve comprises attaching at least one stiffening member to a sleeve, wherein the sleeve is made from brass.

10. The method of claim 6 wherein twisting the at least one stiffening member and the at least one conductor together comprises twisting the at least one stiffening member and the at least one conductor together to about 3 turns per inch.

11. The method of claim 6 wherein soldering a curved tube to a mating connector comprises soldering a curved tube to a mating connector, wherein the mating connector is adapted to mate to a coaxial connector attached to a Behind The Ear (BTE) device, and wherein the mating connector and coaxial connector provide both a mechanical connection and an electrical connection.

12. The method of claim 6 wherein soldering the at least one conductor to at least one terminal of the mating connector to form at least one connection comprises soldering the at least one conductor to at least one circuit including at least one resister, wherein the at least one circuit allows a three wire microphone to operate in a two wire mode.

13. A method of constructing an ITE microphone earhook, comprising:
   attaching at least one conductor to at least one terminal on a microphone to form a first sub-assembly;
   attaching at least one stiffening member to a sleeve to form a second sub-assembly;
   inserting the first sub-assembly into the second sub-assembly, wherein the at least one conductor is guided into the end of the sleeve opposite the at least one stiffening member, and wherein the first assembly is inserted until the end of the microphone opposite the at least one conductor is flush with the end of the sleeve opposite the at least one stiffening member;
   filling the resulting cavity in the sleeve containing the at least one conductor with potting compound;
   allowing the potting compound to cure;
   twisting the at least one stiffening member and the at least one conductor together as a group;
   sliding shrink tubing over the at least one stiffening member and the at least one conductor up to the base of the sleeve, to form the ITE microphone stalk;
   shrinking the shrink tubing;
   attaching a filter to the end of the sleeve opposite the stalk;
   inserting the microphone and stalk assembly, stalk first, through the large opening of a microphone boot;
   soldering a curved tube to a mating connector;
   inserting the stalk into the curved tube;
   positioning the at least one stiffening member against the mating connector to establish the proper length of the stalk;
   soldering the at least one stiffening member to the inside diameter of the mating connector;
   soldering the at least one conductor to the appropriate at least one terminal of the mating connector to form at least one connection;
   potting the volume around the at least one connection with epoxy to cover the at least one connection;
   over molding the mating connector, curved tube, and adjacent end of the stalk with a medical grade PVC to form an ear hook to complete the ITE microphone earhook.

14. The method of claim 13 wherein attaching at least one conductor to at least one terminal on a microphone comprises attaching three conductors to three terminals on a microphone to form a first sub-assembly.

15. The method of claim 13 wherein attaching at least one stiffening member to a sleeve comprises attaching two stiffening members to a sleeve to form a second sub-assembly.

16. The method of claim 13 wherein attaching at least one stiffening member to a sleeve comprises attaching at least one stiffening member to a sleeve, wherein the sleeve is made from brass.

17. The method of claim 13 wherein twisting the at least one stiffening member and the at least one conductor together as a group comprises twisting the at least one stiffening member and the at least one conductor together as a group to about 3 turns per inch.

18. The method of claim 13 wherein inserting the microphone and stalk assembly, stalk first, through the large opening of a microphone boot comprises inserting the microphone and stalk assembly, stalk first, through the large opening of a microphone boot, wherein the boot is made from an elastomer.

19. The method of claim 13 wherein soldering a curved tube to a mating connector comprises soldering a curved tube to a mating connector, wherein the mating connector is adapted to mate to a coaxial connector attached to a Behind The Ear (BTE) device, and wherein the mating connector and coaxial connector provide both a mechanical connection and an electrical connection.

20. The method of claim 13 wherein soldering the at least one conductor to the appropriate at least one terminal of the mating connector to form at least one connection comprises soldering the at least one conductor to at least one circuit including at least one resister, wherein the at least one circuit allows a three wire microphone to operate in a two wire mode.

* * * * *